United States Patent [19]
Vietmeier

[11] Patent Number: 6,143,002
[45] Date of Patent: Nov. 7, 2000

[54] SYSTEM FOR DELIVERING STENTS TO BIFURCATION LESIONS

[75] Inventor: Kristopher H. Vietmeier, Champlin, Minn.

[73] Assignee: Scimed Life Systems, Inc., Maple Grove, Minn.

[21] Appl. No.: 09/129,472

[22] Filed: Aug. 4, 1998

[51] Int. Cl.$^7$ .................................................. A61M 25/01
[52] U.S. Cl. ............................................................. 606/108
[58] Field of Search ............................. 606/108, 198, 606/191; 604/93; 623/1, 12, 1.11, 1.25

[56] References Cited

U.S. PATENT DOCUMENTS

| | | |
|---|---|---|
| 4,730,616 | 3/1988 | Frisbie et al. . |
| 4,896,670 | 1/1990 | Crittenden . |
| 4,994,071 | 2/1991 | MacGregor . |
| 5,143,093 | 9/1992 | Sahota . |
| 5,219,355 | 6/1993 | Parodi et al. . |
| 5,316,023 | 5/1994 | Palmaz et al. . |
| 5,413,581 | 5/1995 | Goy . |
| 5,591,228 | 1/1997 | Edoga . |
| 5,607,444 | 3/1997 | Lam . |
| 5,609,627 | 3/1997 | Goicoechea et al. . |
| 5,613,980 | 3/1997 | Chauhan . |
| 5,617,878 | 4/1997 | Taheri . |
| 5,632,762 | 5/1997 | Myler . |
| 5,632,763 | 5/1997 | Glastra . |
| 5,639,278 | 6/1997 | Dereume et al. . |
| 5,643,340 | 7/1997 | Nunokawa . |
| 5,669,924 | 9/1997 | Shaknovich . |
| 5,720,735 | 2/1998 | Dorros . |
| 5,749,825 | 5/1998 | Fischell et al. . |
| 5,749,890 | 5/1998 | Shaknovich . |
| 5,755,734 | 5/1998 | Richter et al. . |
| 5,755,735 | 5/1998 | Richter et al. . |
| 5,755,770 | 5/1998 | Ravenscroft . |
| 5,755,771 | 5/1998 | Penn et al. . |
| 5,755,772 | 5/1998 | Evans et al. . |
| 5,755,773 | 5/1998 | Evans et al. . |
| 5,755,778 | 5/1998 | Kleshinski . |
| 5,776,101 | 7/1998 | Goy . |
| 5,782,906 | 7/1998 | Marshall et al. . |

FOREIGN PATENT DOCUMENTS

| | | |
|---|---|---|
| 0 479 730 B1 | 4/1992 | European Pat. Off. . |
| 2 678 508 A1 | 1/1993 | European Pat. Off. . |
| 0 686 379 A2 | 12/1995 | European Pat. Off. . |
| WP 95/21592 | 8/1995 | WIPO . |
| WO 96/34580 | 11/1996 | WIPO . |
| WO 96/41592 | 12/1996 | WIPO . |
| WO 97/07752 | 3/1997 | WIPO . |
| WO 97/15346 | 5/1997 | WIPO . |
| WO 97/41803 | 11/1997 | WIPO . |
| WO 98/19628 | 5/1998 | WIPO . |

*Primary Examiner*—Gene Mancene
*Assistant Examiner*—Eduardo C. Robert
*Attorney, Agent, or Firm*—Todd P. Messal

[57] ABSTRACT

A stent deployment catheter includes an elongate catheter shaft having a proximal end, a distal end, and a lumen therethrough. A first stent sheath has a lumen therethrough and an elongate longitudinal opening therein. A second stent sheath also has a lumen therethrough and an elongate longitudinal opening therein. The first and second stent sheaths are disposed at the distal end of the catheter shaft. An elongate actuator is coupled to the first and second stent sheaths and extends to a proximal region of the catheter shaft. The actuator is longitudinally movable relative to the catheter shaft.

18 Claims, 6 Drawing Sheets

SYSTEM FOR DELIVERING STENTS TO BIFURCATION LESIONS

BACKGROUND OF THE INVENTION

The present invention relates to a system for treating vascular disease. More specifically, the present invention relates to a system for deploying a stent in a bifurcation lesion.

Vascular disease currently represents a prevalent medical condition. Typical vascular disease involves the development of a stenosis in the vasculature. The particular vessel containing the stenosis can be completely blocked (or occluded) or it can simply be narrowed (or restricted). In either case, restriction of the vessel caused by the stenotic lesion results in many well known problems caused by the reduction or cessation of blood circulation through the restricted vessel.

A bifurcation is an area of the vasculature where a first (or parent) vessel is bifurcated into two or more branch vessels. It is not uncommon for stenotic lesions to form in such bifurcations. The stenotic lesions can affect only one of the vessels (i.e., either of the branch vessels or the parent vessel) two of the vessels, or all three vessels.

Vascular stents are also currently well known. Vascular stents typically involve a tubular stent which is movable from a collapsed, low profile, delivery position to an expanded, deployed position. The stent is typically delivered using a stent delivery device, such as a stent delivery catheter. In one common technique, the stent is crimped down to its delivery position over an expandable element, such as a stent deployment balloon. The stent is then advanced using the catheter attached to the stent deployment balloon to the lesion site under any suitable, commonly known visualization technique. The balloon is then expanded to drive the stent from its delivery position to its deployed position in which the outer periphery of the stent frictionally engages the inner periphery of the lumen. In some instances, the lumen is predilated using a conventional dilatation catheter, and then the stent is deployed to maintain the vessel in an unoccluded, and unrestricted position.

Self-expanding stents can also be used. Self-expanding stents are typically formed of a resilient material. The resilient material has sufficient resilience that it can be collapsed to the low profile position and inserted within a delivery device, such as a catheter. Once the catheter is placed at the site of the stenotic lesion, the stent is pushed from within the catheter such that it is no longer constrained in its low profile position. The stent, driven by the resilience of the material, expands to a higher profile, deployed position in which its outer periphery frictionally engages the walls of the stenosed vessel, thereby reducing the restriction in the vessel.

While there have recently been considerable advances in stent design and stent deployment techniques, current methods of treating bifurcation lesions are suboptimal, particularly where both downstream branch vessels are affected by the lesion. Current techniques of dealing with such lesions typically require the deployment of a slotted tube stent across the bifurcation. However, this compromises the ostium of the unstented branch.

Further, once the first stent is deployed, the treating physician must then advance a dilatation balloon between the struts of the stent already deployed in order to dilate the second branch vessel. The physician may then attempt to maneuver a second stent through the struts of the stent already deployed, into the second branch vessel for deployment. This presents significant difficulties. For example, dilating between the struts of the stent already deployed tends to distort that stent. Further, deploying the second stent through the struts of the first stent is not only difficult, but it can also distort the first stent. Thus, the current systems used to alternately deploy stents in a bifurcated lesion have significant disadvantages.

SUMMARY OF THE INVENTION

A stent deployment catheter includes an elongate catheter shaft having a proximal end, a distal end, and a lumen therethrough. A first stent sheath has a lumen therethrough and an elongate longitudinal opening therein. A second stent sheath also has a lumen therethrough and an elongate longitudinal opening therein. The first and second stent sheaths are disposed at the distal end of the catheter shaft. An elongate actuator is coupled to the first and second stent sheaths and extends to a proximal region of the catheter shaft. The actuator is longitudinally movable relative to the catheter shaft.

DETAILED DESCRIPTION OF THE PREFERRED EMBODIMENTS

Figure 1:
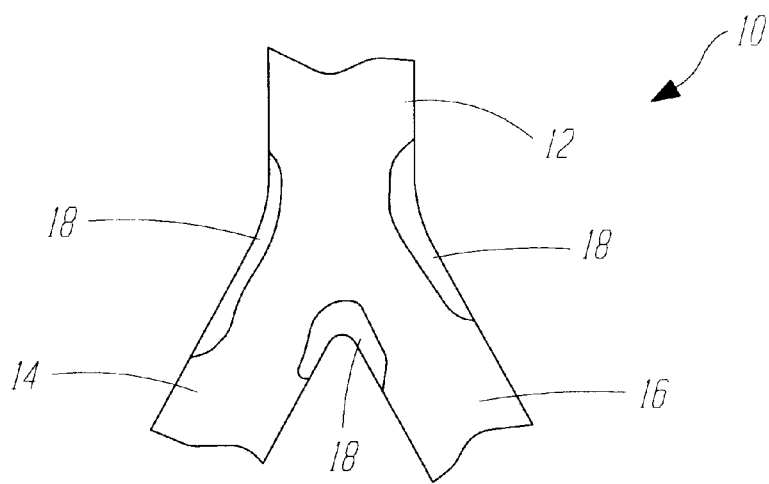
FIG. 1 illustrates typical bifurcation lesion.

FIG. 1 illustrates bifurcation 10 which includes parent vessel 12, first branch vessel 14 and second branch vessel 16. FIG. 1 also illustrates that a bifurcation lesion 18 has developed in bifurcation 10. Lesion 18 extends into both branch vessels 14 and 16, and extends slightly into parent vessel 12 as well. In order to treat bifurcation lesion 18, it may commonly first be predilated with a conventional balloon catheter dilatation device.

Figure 2:
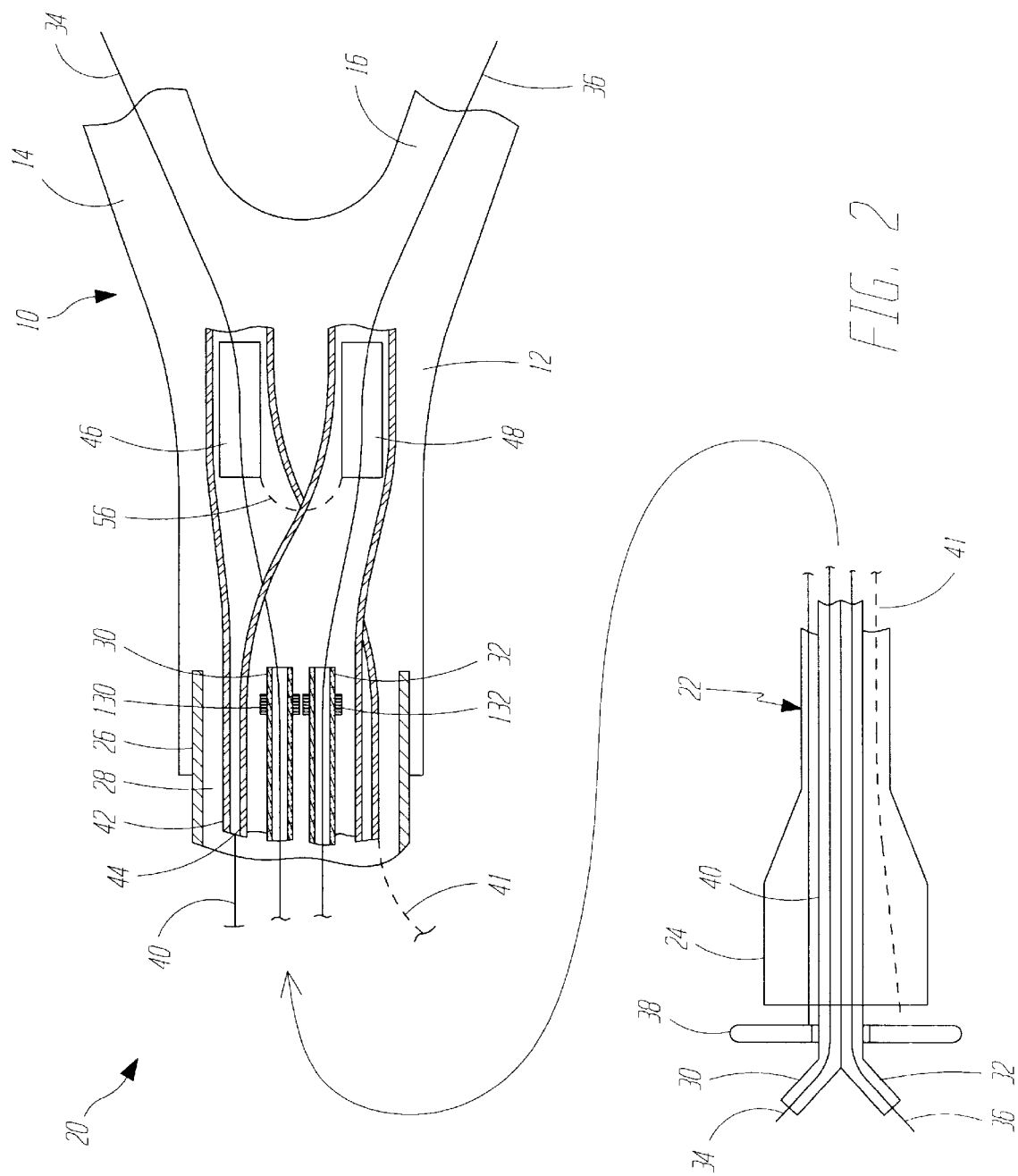
FIG. 2 illustrates one embodiment of a stent delivery system in accordance with one aspect of the present invention.

FIG. 2 illustrates a stent deployment system 20 in accordance with one aspect of the present invention. System 20 includes catheter 22 which has proximal portion 24, distal portion 26 and lumen 28 extending therethrough. In one embodiment, proximal portion 24 includes a conventional proximal hub and a pair of guidewire tubes 30 and 32, which define guidewire lumens extending from the proximal end of catheter 22 to its distal end 26. System 20 is illustrated, in FIG. 2, with a pair of guidewires 34 and 36 extending through the guidewire lumens defined by tubes 30 and 32.

Guidewire tube 30 includes a bumper 130 disposed at its distal end. In a similar manner, guidewire tube 32 includes bumper 132 connected at the distal end thereof. Bumpers 130 and 132 are dimensioned so as to abut the proximal ends of the stents 46 and 48, discussed hereafter.

System 20 also, in one illustrative embodiment, includes proximal actuator 38 which is coupled to actuation wire 40. Actuation wire 40 extends from the proximal end of catheter 22 to a distal region of catheter 22 where it is coupled to a pair of stent deployment sheaths 42 and 44. of course, an additional actuation wire 41 (shown in phantom in FIG. 2) can also be provided, in which case wire 40 is coupled to sheath 42 and wire 41 is coupled to sheath 44.

In either case, each of stent deployment sheaths 42 and 44 has a proximal end and a distal end. A pair of stents, 46 and 48, are illustrated in FIG. 2 positioned within the distal end of sheaths 42 and 44, respectively.

Figure 2A:
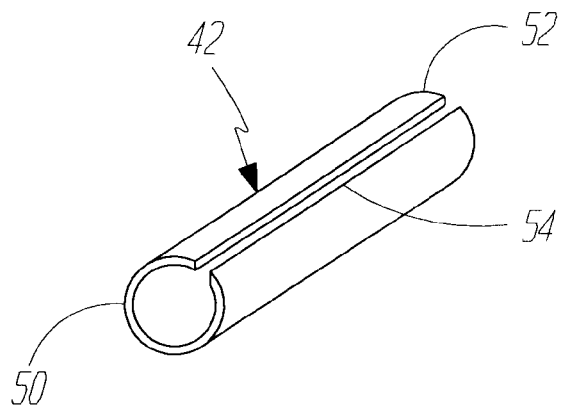
FIG. 2A illustrates a stent deployment sheath in accordance with one aspect of the present invention.

FIG. 2A illustrates one embodiment of stent deployment sheath 42. It will be appreciated that sheath 44 is formed substantially the same as sheath 42. Therefore, only sheath 42 is described in detail in FIG. 2A. Sheath 42 includes proximal end 50 and distal end 52 and is formed substantially cylindrically, but with an elongate slot, or separation, 54 extending from its proximal end 50 to its distal end 52. Sheath 42 has a longitudinal length sufficient to hold stent 46 in a distal portion thereof. Sheath 42 is also sized to slidably fit within lumen 28 of catheter 26. Sheath 42 is preferably formed of a resilient material. The resilience of the material is such that it is sufficient to maintain a stent (such as stent 46) therein in a collapsed, low profile position. However, sheath 42 is also sufficiently resilient that it can be expanded such that slit 54 opens slightly to receive a guidewire and a stent articulation element to accommodate deployment of the stent contained therein, as will be described later in the specification.

Referring again to FIG. 2, sheaths 42 and 44 are generally coaxially disposed at their proximal ends about guidewire tubes 30 and 32. However, the distal ends of sheaths 42 and 44 are not coaxially disposed relative to one another. Rather, the distal end of sheath 44 extends out, through the slot 54 in stent 46 such that the distal ends of sheaths 42 and 44 can independently track guidewires 34 and 36 which extend therethrough.

Guidewire 34 extends out through the distal end of guidewire tube 30, through the slit 54 in sheath 20 44, through stent 46, and into branch vessel 14. Guidewire 36 extends out through the distal end of lumen 32, through stent 48 and sheath 44, and into branch vessel 16.

Stents 46 and 48 are illustrative self-expanding stents. Stents 46 and 48 are thus formed of a resilient material which can be collapsed into a low profile, delivery position, shown in FIG. 2. When in the collapsed position shown in FIG. 2, stents 46 and 48 exert an outward pressure on the inner wall of sheaths 42 and 44, respectively, such that stents 46 and 48 are frictionally held within sheaths 42 and 44 during delivery. Stents 46 and 48 also have sufficient resilience that they self-expand, when removed from sheaths 42 and 44, respectively, to a high profile deployed position. Stents 46 and 48 can be formed as two separate stents, or can optionally be formed as an articulated stent having portions 46 and 48 connected by articulation element 56.

In operation, guidewires 34 and 36 are first advanced to the positions shown in FIG. 2 such that guidewire 34 is advanced across lesion 18 in branch vessel 14 and guidewire 36 is advanced across lesion 18 in branch vessel 16. Stents 46 and 48 are then collapsed to their low profile position and inserted within the distal end of sheaths 42 and 44. Preferably, stents 46 and 48 have been previously collapsed and loaded into position by the manufacturer. Catheter 22 (including sheaths 42 and 44 and guidewire tubes 30 and 32) is either backloaded or preloaded, onto guidewires 34 and 36. Catheter 22 is then advanced within the vasculature to a position just proximal of bifurcation 10, as illustrated in FIG. 2.

Figure 3:
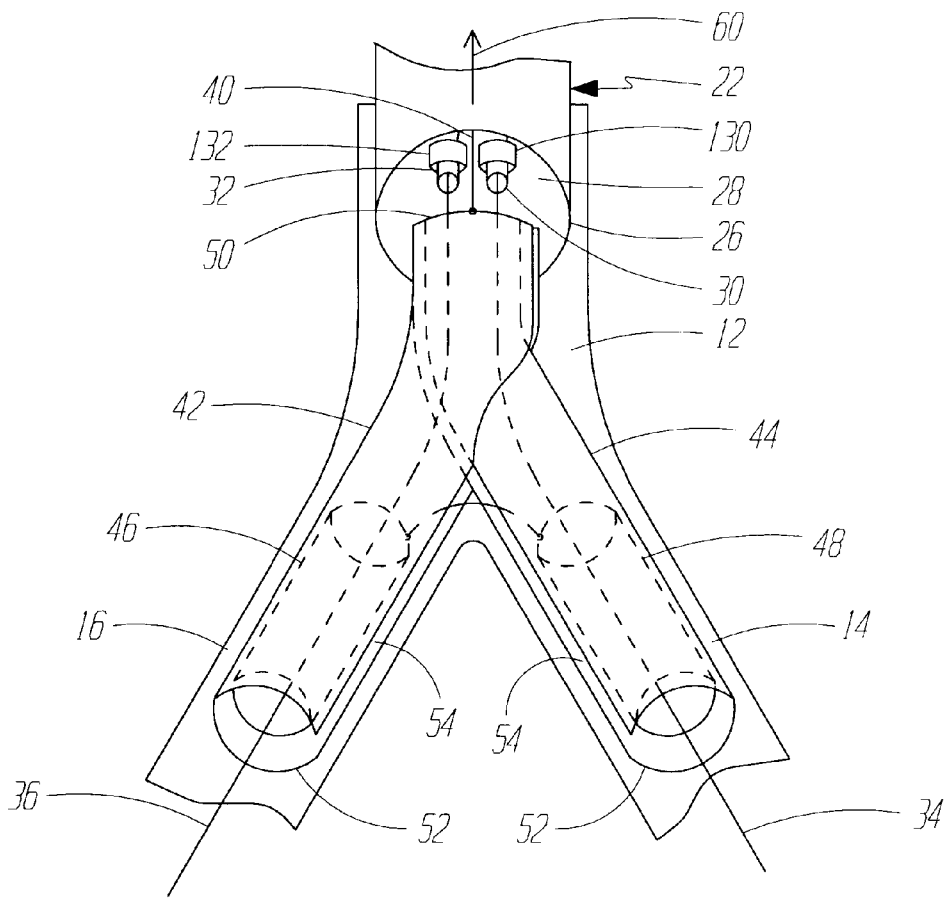
FIG. 3 illustrates placement of a distal end of the stent delivery system shown in FIG. 2 at a site of a bifurcation lesion.

FIG. 3 illustrates the next step in deploying stents 46 and 48 in branch vessels 14 and 16. Catheter 22 is advanced beyond the position shown in FIG. 2 such that the distal ends 52 of sheaths 42 and 44 track along guidewires 36 and 38, respectively. This causes the distal ends 52 of sheaths 42 and 44 to be advanced within branch vessels 14 and 16 to the position shown in FIG. 3. In one preferred embodiment, catheter 22 is advanced distally until the distal ends of guidewire tubes 30 and 32 reside closely adjacent the proximal ends 50 of stents 46 and 48.

Actuator 38 (shown in FIG. 2) is then withdrawn proximally to exert a proximally directed force on actuator wire 40 in a direction indicated by arrow 60. This causes sheaths 42 and 44 to be withdrawn proximally as well. As the sheaths 42 and 44 are withdrawn proximally, bumpers 130 and 132 abut the proximal end of the stents 46 and 48 and thereby maintain their longitudinal position. Thus, as the sheaths 42 and 44 are withdrawn proximally, the guidewire tubes 30 and 32 extend out the distal end of the sheaths 42 and 44 thereby releasing stents 46 and 48 from the low profile, constraint position shown in FIG. 3. Stents 46 and 48 thus expand to frictionally engage the inner walls of branch vessels 14 and 16.

Figure 4:
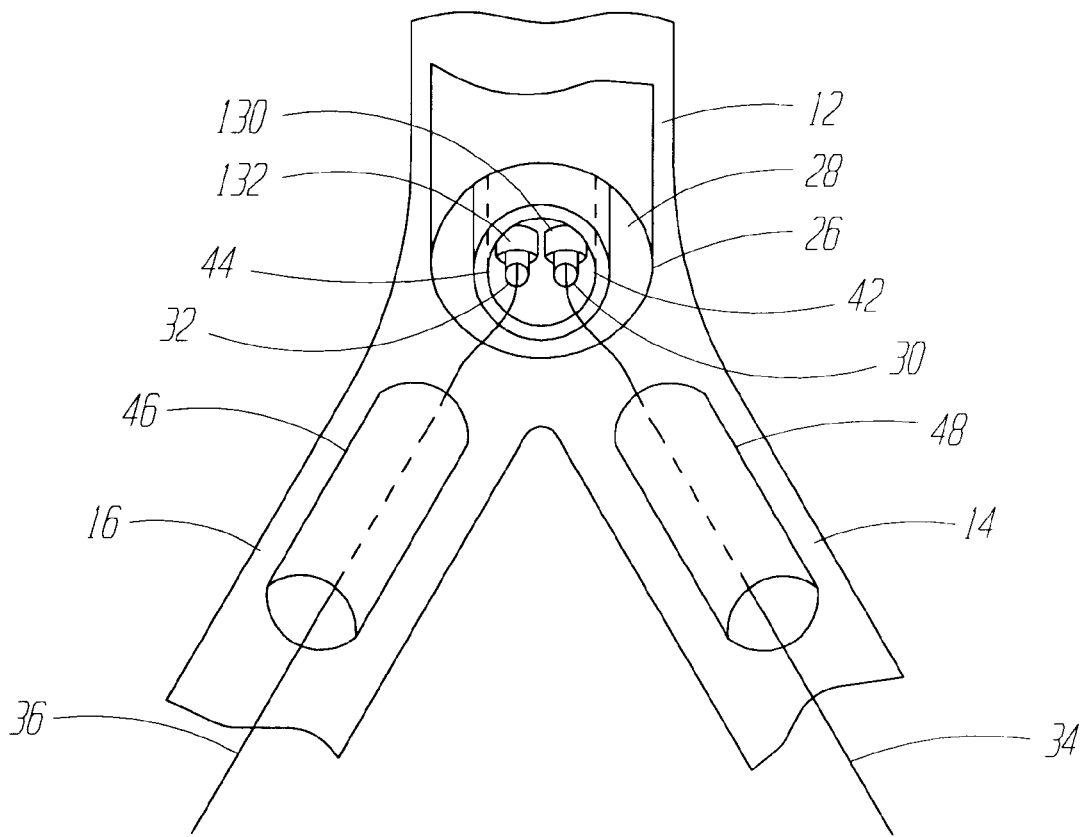
FIG. 4 illustrates deployment of stents in the bifurcation using the system shown in FIGS. 2 and 3.

As sheaths 42 and 44 are withdrawn proximally, the entire longitudinal extent of stents 46 and 48 become unconstrained by the sheaths and thus expand to engage the inner walls of branch vessels 14 and 16, and to be deployed therein, as shown in FIG. 4. Also, as the sheaths are withdrawn proximally, the outer surfaces of sheaths 42 and 44 engage the inner surface of lumen 28. Thus, sheath 44 is forced through the slit 54 in sheath 42 until the two sheaths are fully coaxially disposed. Once in this position, as shown in FIG. 4, catheter 22 is withdrawn over guidewires 34 and 36, leaving stents 46 and 48 deployed in branch vessels 14 and 16.

Figure 5:
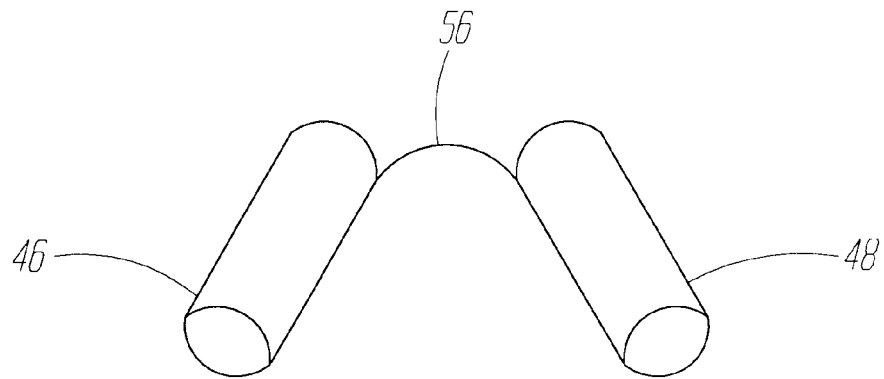
FIG. 5 illustrates an articulated stent.

FIG. 5 illustrates one embodiment of stents in accordance with one aspect of the present invention in which stents 46 and 48 are not separate stents, as shown in previous figures, but are instead portions of an articulated stent connected by articulation element 56. As with stents 46 and 48 in FIGS. 2–4, the stent portions shown in FIG. 5 are also preferably self-expanding stents which can be collapsed to a low profile, delivery position, but are sufficiently resilient such that, when unconstrained, they expand to a higher profile, deployed position. In such an embodiment, sheaths 42 and 44 need not be coaxially disposed within lumen 28 of shaft 26, but can be disposed in a side-by-side manner, as described below.

Figure 6:
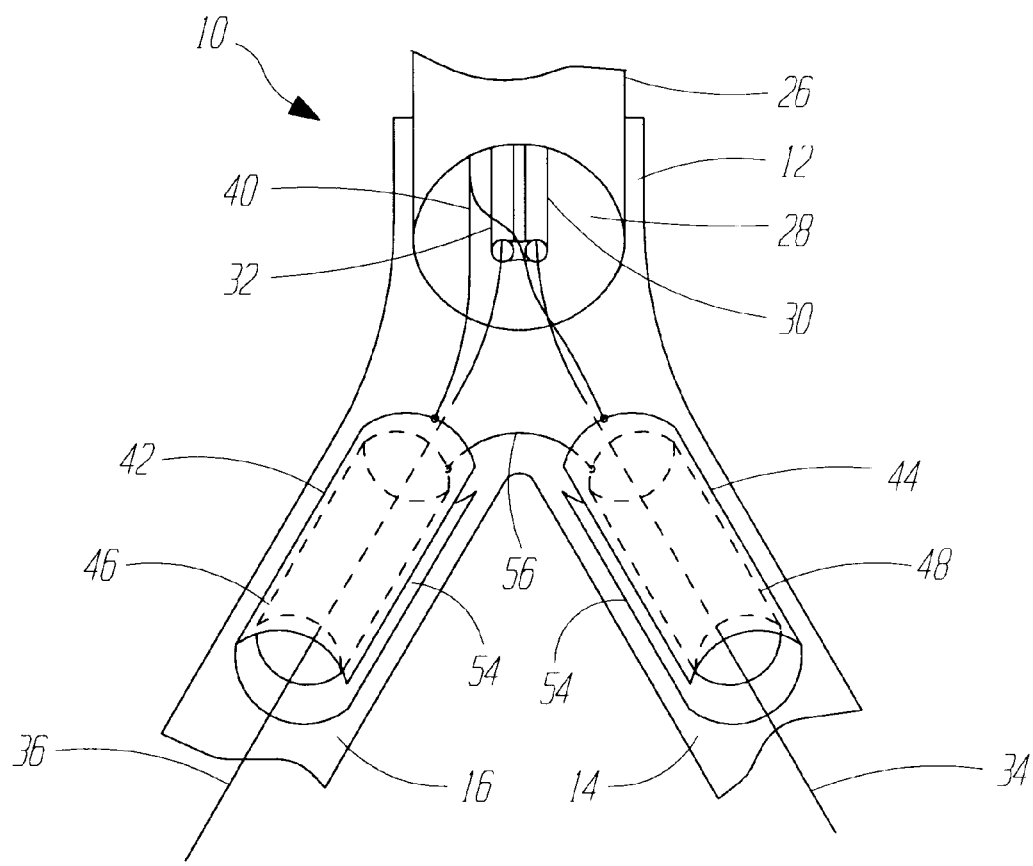
FIG. 6 illustrates the distal end of a stent deployment system located at a bifurcation.

FIG. 6 illustrates an embodiment of the deployment system 62 in accordance with one aspect of the present invention in which the stent being delivered is an articulated stent such as that shown in FIG. 5. A number of the items of system 62 are similar to those of system 20, and are correspondingly numbered. System 62 is prepared and advanced to the position just proximal of bifurcation 10 (shown with respect to system 20 in FIG. 2) in the same fashion as system 20. Catheter 22 is then advanced such that the distal end of sheaths 42 and 44 track over guidewires 36 and 34, respectively, until they reside within branch vessels 16 and 14, respectively. Actuator 38 (shown in FIG. 2) is then withdrawn proximally such that actuator wire 40 is also drawn proximally. This causes sheaths 42 and 44 to be withdrawn proximally, along with stents 46 and 48, until articulation element 56 abuts the distal ends of guidewire tubes 30 and 32. Continued proximal withdrawal of sheaths 42 and 44 causes slits 54, therein, to receive articulation element 56 and any septum, or junction, between guidewire tubes 30 and 32. This allows articulation element 56 to slide within slots 54 as sheaths 42 and 44 are withdrawn proximally, while leaving stents 46 and 48 in place.

Figure 7:
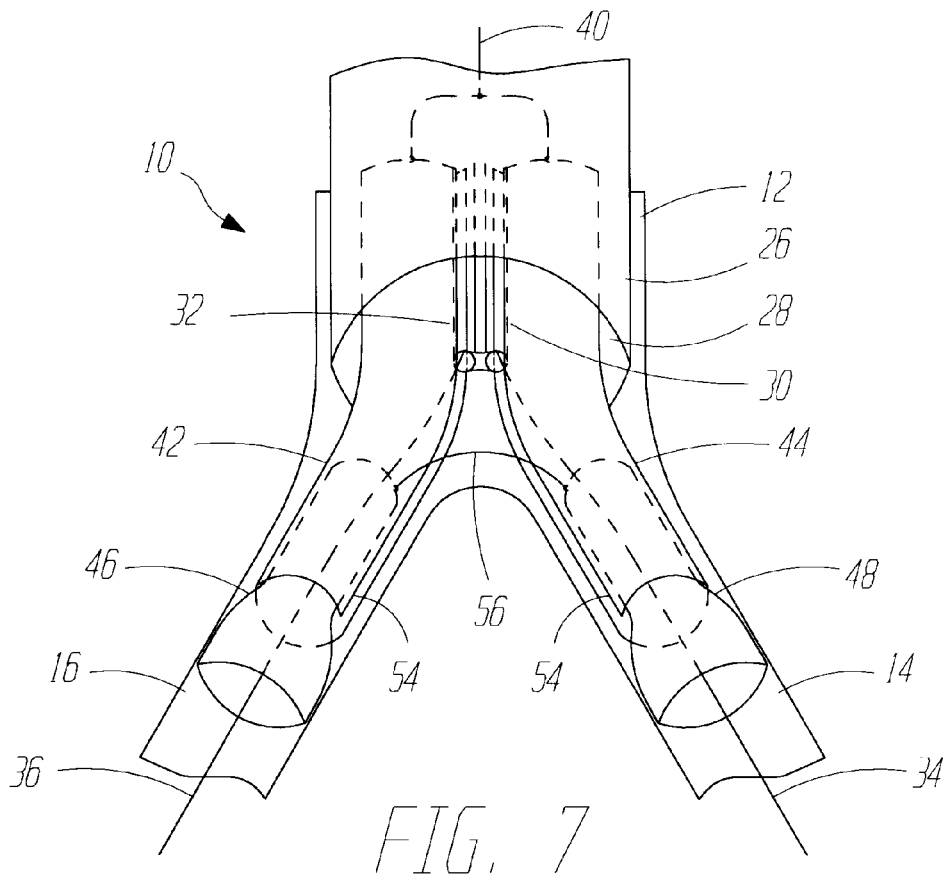
FIG. 7 illustrates deployment of the stents using the system shown in FIG. 6.

FIG. 7 illustrates system 62 with sheaths 42 and 44 withdrawn proximally a short distance, exposing a distal portion of stents 46 and 48 to the inner walls of branch vessels 16 and 14, respectively. Upon being unconstrained by sheaths 42 and 44, stents 46 and 48 self-expand to the higher profile, deployed position.

Figure 8:
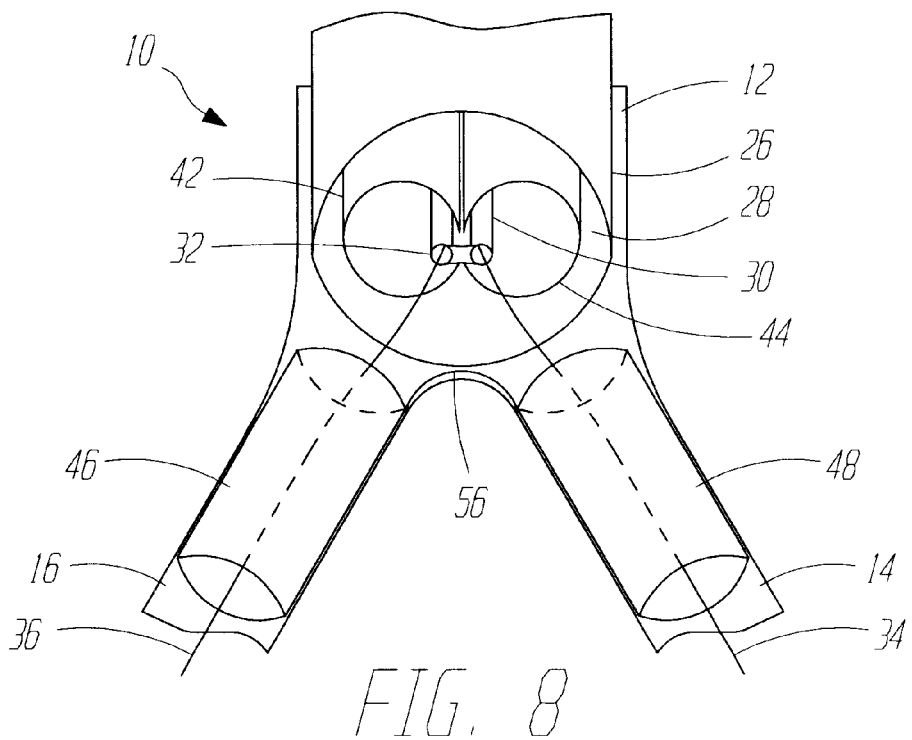
FIG. 8 illustrates an articulated stent positioned in the bifurcation shown in FIGS. 6 and 7.

FIG. 8 illustrates system 62 with sheaths 42 and 44 fully withdrawn within catheter 26 leaving stents 46 and 48 deployed in branch vessels 16 and 14, respectively. It should be noted that sheaths 42 and 44 need not be coaxially arranged, even when withdrawn within shaft 26. Instead, slits 54 simply expand to receive the septum between guidewire tubes 30 and 32 or are otherwise separately longitudinally aligned within shaft 26. Catheter 22 is then withdrawn from the vasculature leaving the deployed stents 46 and 48 in place. Guidewires 34 and 36 are then withdrawn from the vasculature. of course, guidewires 34 and 36 can be withdrawn simultaneously with catheter 22, as well.

Figure 9:
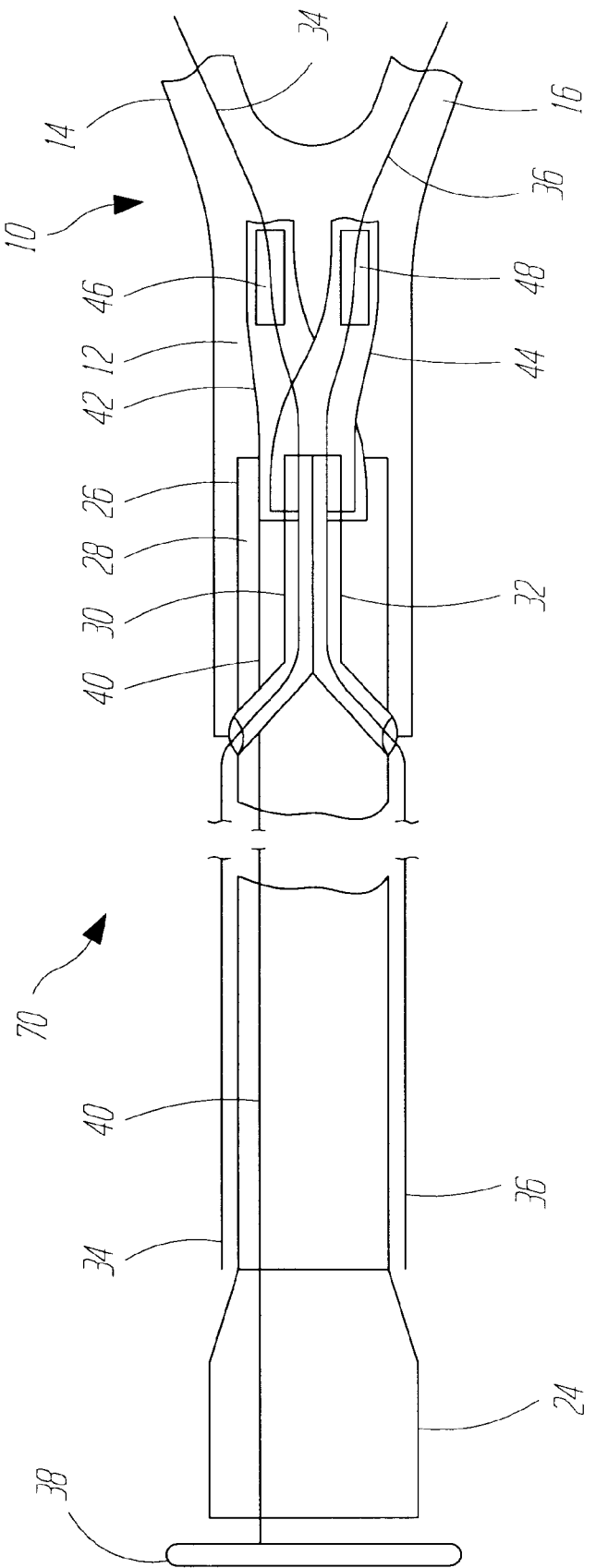
FIG. 9 illustrates another embodiment of a stent deployment system in accordance with one aspect of the present invention.

FIG. 9 illustrates another embodiment of a catheter 70 in accordance with one aspect of the present invention. A number of items are similar to catheter 22 shown in FIG. 2, and are similarly numbered. However, rather than guidewire tubes 30 and 32 extending from a distal end of shaft 26 all the way to a proximal end of catheter 70, guidewire tubes 30 and 32 have proximal openings located in a distal region of shaft 26. Thus, it can be seen that the present invention can be implemented in a single operator exchange type configuration as well.

As can be seen, the present invention provides an improved system and technique for deploying stents at bifurcation lesions. The present invention provides deployment sheaths configured to allow convenient and accurate placement of stents, over two guidewires, without removing the guidewires from the vasculature, and without a great deal of excess manipulation required by the treating physician.

Although the present invention has been described with reference to preferred embodiments, workers skilled in the art will recognize that changes may be made in form and detail without departing from the spirit and scope of the invention.

What is claimed is:

1. A stent deployment system, comprising:
   a catheter having a proximal end, a distal end, a delivery lumen extending through at least a distal portion thereof, and first and second guide wire lumens extending at least through the distal portion thereof;
   a first sheath portion including a first tubular wall having a proximal end, a distal end and a longitudinal opening extending proximally from the distal end thereof, the longitudinal opening being sized to receive a guide wire therethrough, the first tubular wall having an inner periphery sized to receive a collapsible stent in a collapsed position;
   a second sheath portion including a second tubular wall having a proximal end, a distal end and a longitudinal opening extending proximally from the distal end thereof, the longitudinal opening being sized to receive a guide wire therethrough, the second tubular wall having an inner periphery sized to receive a collapsible stent in a collapsed position; and
   an actuator, coupled to the first and second sheath portions, longitudinally movable relative to the catheter, comprising
      a first elongate member coupled to the first sheath portion and extending through the delivery lumen to a proximal end thereof and
      a second elongate member coupled to the second sheath portion and extending through the delivery lumen to a proximal end thereof.

2. The stent deployment system of claim 1 wherein the first and second tubular walls are sized to receive first and second stent portions of an articulated stent therein, and wherein the longitudinal openings in the first and second tubular walls are sized to receive an articulation element connecting the first and second stent portions.

3. The stent deployment system of claim 1 wherein the longitudinal opening in the first tubular wall is formed to receive at least a portion of the second tubular wall therethrough upon exertion of an actuation force on the actuator sufficient to cause the first and second sheath portions to move within the delivery lumen.

4. The stent deployment system of claim 1 and further comprising:
   a first guidewire extending through the first guidewire lumen and through the longitudinal opening in the first tubular wall and out the distal end of the first tubular wall.

5. The stent deployment system of claim 4 and further comprising:
   a second guidewire extending through the second guidewire lumen and through the longitudinal opening in the second tubular wall and out the distal end of the second tubular wall.

6. A method of stenting a bifurcation having a parent vessel and first and second branch vessels, comprising;
   positioning a first guide wire in the first branch vessel;
   positioning the second guide wire in the second branch vessel;
   providing a catheter having a delivery lumen and first and second guide wire lumens;
   providing first and second sheaths, each having a longitudinal opening therein and a stent retaining lumen with a collapsible stent therein;
   positioning the first sheath over the first guide wire such that the first guide wire extends through the longitudinal opening in the second sheath, through the stent and out the distal end of the first sheath and such that the proximal end of the first sheath is within the distal end of the delivery lumen;
   positioning the second sheath over the second guide wire such that the second guide wire extends through the longitudinal opening in the first sheath, through the stent and out the distal end of the second sheath and such that the proximal end of the second sheath is within the distal end of the delivery lumen;
   advancing the catheter over the first and second guide wires until the distal ends of the first and second sheaths are in the first and second branch vessels, respectively; and
   exerting a proximally directed force on an actuator element, the actuator element coupled to a proximal end of the wire, the wire coupled to the first and second sheaths through the delivery lumen.

7. The method of claim 6 and further comprising:

withdrawing the catheter with the first and second sheaths in the delivery lumen.

8. A stent deployment catheter, comprising:

an elongate catheter shaft having a proximal end, a distal end and a lumen therethrough;

a first stent sheath having a lumen therethrough and an elongate longitudinal opening therein and being disposed at the distal end of the catheter shaft;

a second stent sheath having a lumen therethrough and an elongate longitudinal opening therein and being disposed at the distal end of the catheter shaft; and an elongate actuator comprising, a first elongate actuator member coupled to the first stent sheath and a second elongate actuator member coupled to the second stent sheath, the actuator coupled to the first and second stent sheaths and extending to a proximal region of the catheter shaft, the actuator being longitudinally moveable relative to the catheter shaft.

9. The stent deployment catheter of claim 8 wherein proximal ends of the first and second stent sheaths are coaxially positioned within the distal end of the catheter shaft.

10. The stent deployment catheter of claim 8 wherein proximal ends of the first and second stent sheaths are positioned in side-by-side arrangement within the distal end of the catheter shaft.

11. The stent deployment catheter of claim 8 wherein the first and second stent sheaths are sized to receive first and second collapsible stent portions therein, respectively, wherein the first and second stent portions are connected by an articulation element and wherein the longitudinal openings in the first and second stent sheaths are sized to receive the articulation element therethrough.

12. The stent deployment catheter of claim 8 wherein the catheter shaft comprises:

first and second guidewire lumens extending at least through the distal end thereof.

13. The stent deployment catheter of claim 12 wherein the longitudinal openings of the first and second stent sheaths are sized to receive first and second guidewires therethrough.

14. The stent deployment catheter of claim 13 wherein the longitudinal opening in the first stent sheath is expandable to receive an outer periphery of the second stent sheath therethrough.

15. A method of stenting a bifurcation having a parent vessel and first and second branch vessels, comprising;

positioning a first guide wire in the first branch vessel;

positioning the second guide wire in the second branch vessel;

providing a catheter having a delivery lumen and first and second guide wire lumens;

providing collapsible stents comprise first and second portions coupled to one another by an articulation element;

providing first and second sheaths, each having a longitudinal opening therein and a stent retaining lumen with a collapsible stent therein, and wherein providing first and second sheaths comprises providing the stent portions in the first and second sheaths such that the articulation element extends through the longitudinal openings in the first and second sheaths;

positioning the first sheath over the first guide wire such that the first guide wire extends through the longitudinal opening in the second sheath, through the stent and out the distal end of the first sheath and such that the proximal end of the first sheath is within the distal end of the delivery lumen;

positioning the second sheath over the second guide wire such that the second guide wire extends through the longitudinal opening in the first sheath, through the stent and out the distal end of the second sheath and such that the proximal end of the second sheath is within the distal end of the delivery lumen;

advancing the catheter over the first and second guide wires until the distal ends of the first and second sheaths are in the first and second branch vessels, respectively; and withdrawing the first and second sheaths proximally over the first and second guide wires and into non-coaxial arrangement within the delivery lumen such that the longitudinal openings in the first and second sheaths receive the first and second guide wire lumens and slide thereover as the first and second sheaths are withdrawn proximally and the articulation element passes distally through the longitudinal openings in the first and second sheaths as the first and second sheaths are withdrawn to deploy the stents from within the stent retaining lumens.

16. The method of claim 15 wherein proximally withdrawing further comprises:

withdrawing the first and second sheaths into coaxial arrangement within the delivery lumen.

17. The method of claim 16 wherein proximally withdrawing further comprises:

withdrawing the first and second sheaths into the delivery lumen such that the longitudinal opening in the first sheath receives an outer periphery of the second sheath therein.

18. The method of claim 17 wherein proximally withdrawing further comprises:

withdrawing the first and second sheaths such that the second sheath passes through the longitudinal opening in the first sheath as the first and second sheaths are withdrawn until the second sheath resides coaxially within the first sheath in the delivery lumen.

* * * * *